United States Patent
Thiel et al.

(10) Patent No.: US 8,890,709 B2
(45) Date of Patent: Nov. 18, 2014

(54) DISPLAY OF A SYSTEM STATE OF A TREATMENT DEVICE FOR MICROSCOPIC SAMPLES

(75) Inventors: Michael Thiel, Stutensee (DE); Hermann Ulbrich, Bad Schönborn-Mingolsheim (DE); Martin Zwicklowsky, Östringen (DE); Michael Erben, Oberhausen-Rheinhausen (DE); Michael Rapp, Oftersheim (DE); Stefan Künkel, Karlsruhe (DE); Udo Herrmann, Leimen (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 262 days.

(21) Appl. No.: 13/509,421

(22) PCT Filed: Nov. 15, 2010

(86) PCT No.: PCT/EP2010/067514
§ 371 (c)(1),
(2), (4) Date: Feb. 18, 2013

(87) PCT Pub. No.: WO2011/058181
PCT Pub. Date: May 19, 2011

(65) Prior Publication Data
US 2013/0141246 A1    Jun. 6, 2013

(30) Foreign Application Priority Data

Nov. 13, 2009  (DE) .................. 10 2009 046 695

(51) Int. Cl.
*G08B 5/36* (2006.01)
*G01N 1/36* (2006.01)
*G01N 35/00* (2006.01)

(52) U.S. Cl.
CPC .. *G08B 5/36* (2013.01); *G01N 1/36* (2013.01); *G01N 2035/00891* (2013.01)
USPC ............. 340/815.67; 340/815.72; 340/815.86

(58) Field of Classification Search
CPC ........................................................ G08B 5/36
USPC .......................... 340/815.67, 815.72, 815.86
See application file for complete search history.

(56) References Cited

U.S. PATENT DOCUMENTS

| | | | |
|---|---|---|---|
| 7,118,564 B2 * | 10/2006 | Ritchie et al. ................... | 606/16 |
| 7,850,912 B2 * | 12/2010 | Favuzzi et al. .................. | 422/63 |
| 2007/0243626 A1 | 10/2007 | Windeyer et al. | |

FOREIGN PATENT DOCUMENTS

| | | |
|---|---|---|
| CN | 1595167 A | 3/2005 |
| DE | 199 33 924 | 11/2000 |
| DE | 103 37 236 | 3/2005 |
| DE | 10 2004 036 578 | 3/2006 |
| DE | 601 13 073 | 8/2006 |

(Continued)

*Primary Examiner* — Tai T Nguyen
(74) *Attorney, Agent, or Firm* — Hodgson Russ LLP

(57) ABSTRACT

The invention relates to a method of displaying a system state of an automatic treatment device, a corresponding display system which is configured for carrying out the method, and a treatment device equipped with the display system. At least one system parameter (121, 122, 123) is determined, the at least one determined (120) system parameter (121, 122, 123) is evaluated on the basis of evaluation criteria, the system state is evaluated on the basis of the at least one evaluated (130) system parameter (121, 122, 123), and the evaluated (140) system state is displayed by a traffic light function (175).

18 Claims, 2 Drawing Sheets

(56) References Cited

FOREIGN PATENT DOCUMENTS

| | | |
|---|---|---|
| DE | 10 2006 022 740 | 11/2007 |
| DE | 10 2006 030 895 | 1/2008 |
| EP | 1569181 | 8/2005 |
| EP | 1919132 | 5/2008 |
| WO | 00/36393 | 6/2000 |

* cited by examiner

DISPLAY OF A SYSTEM STATE OF A TREATMENT DEVICE FOR MICROSCOPIC SAMPLES

CROSS REFERENCE TO RELATED APPLICATIONS

The present application is the U.S. National Stage of International Application No. PCT/EP2010/067514 filed Nov. 15, 2010, which claims priority of German Application No. 10 2009 046 695.9-52 filed Nov. 13, 2009. The present application claims priority benefit of International Application No. PCT/EP2010/067514 and German Application No. 10 2009 046 695.9-52.

FIELD OF THE INVENTION

The present invention relates to a method of displaying a system state of an automatic treatment device.

BACKGROUND OF THE INVENTION

Treatment devices of this kind for microscopic samples are known per se from the prior art. They might be, in particular, an automatic embedding device, an automatic staining device and/or an automatic covering device. The treatment device may consequently consist of one or more such devices. In the simplest case, the treatment device therefore consists for example of an automatic embedding device which prepares a sample for a subsequent microtome section in a plurality of process steps. A tissue processor of this kind for biological or histological samples is known from DE 10 2005 057 191 A1. The same applies to an automatic staining device and an automatic covering device. These devices may also be combined to form one piece of equipment. A treatment device for the purposes of the present application may thus also be a combined apparatus of this kind, i.e. a combined automatic staining and covering device, for example, in which a sample is processed in a number of process steps, while in this case the samples first pass through the automatic staining device and then through the automatic covering device for applying cover slips to the stained sample.

With regard to the structure and mode of operation of automatic staining and covering devices per se and in combination with one another, reference is explicitly made to German Patent no. DE 101 44 989 B4 which relates to a system for processing specimens mounted on slides for subsequent microscopic examination, this system comprising an autonomously operating automatic staining device for staining the specimens, which is configured separately in a housing, a plurality of slides being arranged in a rack and passing through the staining process in this rack. In addition, the system comprises a transporting device for transporting the rack within the automatic staining device and a separately configured and autonomously operating automatic covering device for applying cover slips to the stained specimens. The automatic staining device and automatic covering device are arranged side by side and contain lateral openings facing one another, through which a transporting device configured as a robot arm is able to transfer a rack from the automatic staining device directly into the automatic covering device. Regarding the exact sequence of the independent process steps through which a microscopic sample passes, reference is once again made to this specification.

Similar systems for staining and covering microscopic samples on slides are known from DE 101 44 042 A1 and from DE 201 22 727 U.

Embedding devices, also known as automatic embedding devices or tissue processors, are used in routine clinical diagnostics for preparing samples for microscopic examination.

To obtain thin, uniform microtome sections in histopathology, the material that is to be examined must have stability and a uniform consistency or strength. For this reason, tissue infiltration with hot paraffin wax (hereinafter also generally referred to as "paraffin") is frequently carried out.

As paraffin is insoluble in water, tissue (for example formalin-fixed) is first dehydrated as gently as possible in an increasing alcohol series (with an increasing concentration of methanol or ethanol). After the dehydration the alcohol from the last dehydration step, which is as anhydrous as possible, is removed using a so-called intermedium (e.g. xylene or a xylene mixture) that is particularly readily miscible with paraffin and additionally absorbs the last remnants of water. The intermedium is then replaced by hot paraffin wax, often by vacuum infiltration.

The paraffin-impregnated pieces of tissue can then be processed into cuttable paraffin blocks, then sliced and transferred onto slides. After deparaffination, staining, covering, etc., the sections are available for examination under a microscope.

A tissue processor which allows substantially automatic processing of samples is shown and described in the Leica publication "Leica ASP 300", Leica Microsystems NuBloch GmbH, Order No. 0704-2-1-103, 04/2001. The tissue processor comprises a retort as the processing station for the samples. The retort is connected to a number of standardised reagent storage containers via a system of tubes or pipes. The respective reagents can be automatically pumped from the storage containers into the retort and back by a pumping system with an electronic control.

Even though the present invention is described within the scope of this application predominantly in relation to paraffin infiltration, it is also suitable for other infiltration methods, for example for embedding in synthetic resin.

The embedding process described previously has a number of critical steps or process variables.

As already mentioned, the residual water in the tissue sample that is to be embedded has to be removed as completely as possible before the infiltration, on account of the poor miscibility of water and paraffin wax, as otherwise the cuttability and sample quality would be adversely affected. However, in practice, water is often entrained from the less concentrated stages of the alcohol gradient into the pure alcohol of the final dehydration stage. Also, the final alcohol stage often contains residual water because of the hygroscopic properties of ethanol, for example.

Certainly, residual water can be partially removed from the tissue samples by the intermedium, as already mentioned. However, in the interests of the highest possible reproducibility and process certainty, care must be taken to ensure that the desired concentrations of the components of the alcohol series are adhered to as accurately as possible. For this purpose, as disclosed in the as yet unpublished applications DE 10 2008 054 071 and DE 10 2008 054 066, thereof may be a concentration and/or purity of a process medium and/or a characteristic property determined.

Xylene which is frequently used as an intermedium is flammable and is harmful to health when absorbed through the skin and airways. In a volume of 1-8% in air, xylene forms explosive mixtures. Xylene contamination from the intermedium used must therefore be kept to a minimum as far as possible. Entrainment problems may also occur during the transfer from the intermedium to the infiltration medium, leading to an increasing xylene concentration in the paraffin wax used subsequently.

When the embedded sample is taken out of the tissue processor at the end of the treatment the user is therefore exposed to possibly harmful xylene vapours. Too high a xylene concentration in the infiltration medium can also adversely affect the sample quality and subsequent cuttability.

Therefore, every effort is made to minimise the xylene concentration in the paraffin, at least in the sample removed at the end. This can be done, for example, using a process for processing tissue samples in which, between the xylene or intermedium treatment step and the treatment of the tissue samples with a carrier material (such as paraffin wax), a carrier material protective reagent is used in which the intermedium and carrier material are miscible (cf. on this subject the as yet unpublished application DE 10 2009 025 574).

Moreover, a process can also be used for this purpose in which carrier material or materials of different degrees of purity are used for different infiltration steps. The carrier material with the highest purity (i.e. with the lowest contamination by the intermedium) is used at the end (cf. on this subject the as yet unpublished application DE 10 2008 039 875).

Exposure of the user to harmful effects from process media and the like may, for example, also be avoided by adopting physical safety measures (cf. on this subject for example the as yet unpublished application DE 2008 039 876).

On the basis of the characteristic values or process parameters explained hereinbefore, for example a concentration of an alcohol solution or a temperature of the paraffin, the expert user can theoretically judge whether the embedding device is in a functional state. However, as far as the routine user is able to tell, if at all, such a judgement in current tissue processors is difficult and laborious.

With the embedding devices currently available for microscopic samples, in the event of a fault an error code is entered into an error protocol. The user has to select (call up) this error code in software, generally using sub-menus, and then decide whether measures are to be taken, and if so which ones. However, such an evaluation can only be carried out by trained staff with their specialist knowledge. Searching through sub-menus for an error code proves to be laborious and complicated.

For the user, the error detection described above is not very user-friendly. Therefore, in routine operation the functional state of the embedding device is often ignored, which may lead to a deterioration in the sample quality, adverse health effects and/or damage to the equipment.

There is a need for a user friendly display of system states of automatic treatment devices for microscopic samples based on detected system parameters enabling a user to react quickly.

SUMMARY OF THE INVENTION

Against this background the present invention provides a method of displaying a system state of an automatic treatment device having a plurality of process steps for microscopic samples based on system parameters of the treatment device, a display system which is configured for carrying out the method, and a corresponding treatment device for microscopic samples.

According to the invention, a method is proposed in which, in order to display a system state of an automatic treatment device for microscopic samples on the basis of system parameters of the treatment device, first of all at least one system parameter is determined, then at least one of the system parameters determined is evaluated and on the basis of at least one evaluated system parameter, an evaluation of the system state is carried out. The system state evaluated is then displayed by means of a traffic light function preferably having a plurality of display states, the display spanning the process steps.

By a "display spanning the process steps" is meant, within the scope of the present application, a display which does not take place specifically for each process step of the treatment device. Rather, the display of the evaluated system state takes place at a higher level than the plurality of process steps. For example, in the event of a fault, a display symbol (for example a red warning triangle) is displayed, so that the user can immediately tell that the treatment device is in a defective state. On the display, a location is preferably exclusively reserved for the display symbol. Thus the user does not have to select various sub-menus associated with the process steps in order to be able to check whether the treatment device is in a defective or functional state.

By a "display spanning the process steps" is meant, in an automatic treatment device which comprises a plurality of automatic devices or processors, for example the automatic embedding and/or automatic staining device and/or automatic covering device already mentioned, that the system state of the multipart treatment device is being displayed. In other words it is not necessary to equip each individual piece of apparatus such as the automatic embedding, staining or covering device, with a traffic light function, but it is sufficient and convenient to provide a single traffic light function on one of the pieces of equipment or at another suitable location, to cover all the equipment.

Within the scope of the present application the terms "automatic device" and "processor" should be treated as equivalent. Microscopic samples pass through a number of process steps in each automatic device; the same is true of treatment devices which contain a number of automatic devices in combination.

The present invention provides the user of an automatic treatment device for microscopic samples with rapid and directly useable information as to whether the equipment in question is in an operational state.

Software for the above-mentioned treatment devices is generally organised into screen pages which correspond for example to specific treatment or processing steps and/or system components. Thanks to the invention an error button which is visible and accessible on each screen page can be displayed as a means of indicating a system state that has been evaluated, this display being provided with a traffic light function. This comprises the colours or display states "red", "amber" and "green", for example, corresponding to three different evaluation categories of system states. If the error button is in the first display state, "green", the user can assume that the system is operating without fault. If "amber" is displayed, there are errors or faults present but no immediate action is required. However, when "amber" is shown a user should for example bear in mind that in the near future either parameters will have to be changed on the equipment, process media used will have to be replaced or a service function, such as for example an automatic cleaning process, will have to be initiated.

In contrast to the prior art, in which, as already mentioned, an entry in an error protocol has to be searched, identified and interpreted, with considerable effort, using the present invention a user, even with no special knowledge, will be able to judge purely intuitively whether the corresponding system is operating without any fault. If there are faults, i.e. for example in the event of a display such as "amber" or "red", the user can then consult an expert or analyse the underlying problem himself and react to it.

If the traffic light function is provided in the form of an error button on one or each screen page, the user can select this button for example by clicking on it and will then receive information as to the system state evaluated, such as for example a detailed analysis of the underlying problem or problems, and/or he will be guided into the corresponding sub-menu which indicates the process step causing problems. The error button may also be configured separately, for example as a button on the apparatus which flashes (red) for example when there is a problem or fault. The error button embodies a display and input means which provides interactivity with the user.

The user can then carry out a change in system parameters, for example software-based, while it may be advantageous to have a classification of users into service levels with graduated information and interaction permissions on the basis of user identification. In this context, it may also be convenient, for example, to activate a remote diagnosis function by means of which the user tasks a central service centre (service provider and/or manufacturer) with the detailed diagnosis or maintenance of the system, possibly on-line.

If the traffic light function is configured in the form of the said error button or another display symbol on a screen display, this may be, for example, a warning triangle or a warning circle. If the system state is classified in two or more evaluation categories, corresponding colours or shading may be used. For example, the error button or display symbol may only show up in the event of a problem, a less critical system state being displayed for example in a first colour (grey or amber), whereas a critical system state is displayed in a second colour (such as red, for example). As already mentioned, an error button of this kind may be selected, whilst if a sensor screen (touchscreen) is used as the screen display the error button can be selected by simply touching it with the user's finger or with another inputting means. If the error button is selected, as already mentioned, error information and/or the process step causing the problem is displayed. In particular, in the latter case, the user is guided, in an advantageous embodiment, to the corresponding sub-menu, by means of which the user can rapidly decide which steps are needed to overcome the problem or fault.

The present invention includes the feature that at first at least one system parameter of the treatment device is determined. Advantageously this is a system-critical parameter which, in the event of a fault, could lead to failure of the system, damage to a sample that is to be processed and/or adverse effects on the health of the user.

The system parameters determined, which are preferably detected by means of sensors, are then evaluated on the basis of predefined evaluation criteria. The evaluation criteria may immediately lead to a classification of the system parameters, if for example a grade of criticality for individual system parameters is determined in accordance with previously defined criticality stages. Thus, in the event that a determined system parameter could lead to damage to the treatment device, this parameter could be categorised in the "high" criticality grade in the event of a fault. Other parameter deviations, for example slightly exceeding a threshold (see below) could be assigned to the "less critical" category.

The system parameters are preferably evaluated by comparing them with desired or threshold values which have previously been defined for example by the user or manufacturer of the equipment. In particular, these may also be application- or sample-specific desired or threshold values. For example, depending on the samples processed, the deviations in the parameters may be graded strictly or less strictly. For example if it is a particularly delicate and irreplaceable material, a system error or a deviation in the parameter which would normally only lead to a classification of "less critical" might be graded as "critical".

On the basis of the system parameters which have been evaluated and/or correspondingly classified individually, in groups or as a whole, within the scope of the evaluation, the system state is now evaluated on the basis of at least one of the evaluated system parameters. Advantageously this may be an evaluation on the principle of the most critical error, whilst a deviation in the parameter evaluated as "critical" within the scope of the evaluation leads to evaluation of the system state as "critical". In particular, the evaluated parameters may also be subjected to an integrated consideration; thus, for example, on the basis of a number of errors or parameter deviations which are of themselves less critical but which, by their accumulative effect, could have an adverse effect on the overall system, the overall state may be evaluated as "critical".

Depending on the system state thus evaluated, the evaluated state is displayed, as already mentioned, in the form of a traffic light function, the traffic light function comprising display states.

Particularly advantageously, as already mentioned, the evaluation of the system state comprises a classification of the system state into at least two evaluation categories. In the simplest case these are the evaluation categories "uncritical" or "error-free" and "critical" or "error". Alternatively, there may be no display of an uncritical or error-free state. In this case it is advisable to define at least two evaluation categories, namely "less critical" or "problematic" and "critical" or "error". However, it should be understood that the method according to the invention, as explained further hereinafter, may also be used for fine classification into as many gradations as desired, while individual criticality stages may also be combined in groups.

It is particularly advantageous if the display of the system state is provided by means of a traffic light function comprising a number of display states that corresponds to the number of evaluation categories. By means of this representation, as already mentioned, the system state can be notified to a user particularly easily and quickly, without the user having to analyse the evaluation categories and/or parameters that underlie the notification.

It is particularly advantageous to use a traffic light function with display states which correspond to the displayed colours, particularly red, amber and green, and/or shades of grey. By means of a function of this kind, which is immediately comprehensible to a user, even in critical situations, and is familiar from everyday life, it is possible to obtain a very simple and easily understood conversion of the system evaluation in the form of "uncritical" or "error free" into "green", "less critical" as "amber" and "critical" or "error" into "red". Alternatively, a non-critical or error-free state may not be displayed. Furthermore, amber may be replaced by a light grey and/or red may be replaced by a darker grey or black. Obviously, other colours or shades of grey may be assigned to the display state mentioned. Finally, shading and/or geometric shapes may be used additionally or alternatively.

Advantageously, the display states may encompass further states. A corresponding traffic light function is therefore usefully equipped with display states by means of which intermediate states can be represented. Advantageously, this may be done, for example, by means of flashing and/or the simultaneous display of several colours, displays of mixed or intermediate colours or intermediate shades of grey. Thus, for example, a traffic light function with a flashing red display may be used to indicate a particularly critical state or which requires immediate measures to be taken in order to prevent damage. An "amber/green" state may indicate a state that will possibly occur in the near future but which does not require any immediate action. If, for example as a result of system faults, communication problems or improbable sensor values, it is not possible to determine a system parameter or carry out an evaluation or assessment, this may be indicated, for example, by all three colours red, amber and green flashing and/or by the simultaneous display of these colours ("undefined system state"). Intermediate values between two of the three stages can be signalled simultaneously by the display of both colours or the corresponding mixture of colours.

It is particularly advantageous to use the method in a treatment device in which a purity and/or a concentration of at least one process medium used is determined as at least one system parameter. A treatment device of this kind is, more particularly, an embedding device and/or an automatic staining device.

By "process medium" are meant, for example, all the solutions used in an embedding device, such as the alcohol/water mixtures of different concentrations, xylene, liquid paraffin wax, formalin and the like. As already mentioned, the entrainment of water into the higher-grade alcohol solutions or the entrainment of xylene into a paraffin wax is critical in embedding devices, for example, and can be detected by the present invention and notified to the user. In an automatic staining device, the term "process medium" would refer to the corresponding staining agents; in an automatic covering device this would mean the cover slips and optionally adhesives.

Particularly advantageously, the process also comprises determining the age and/or a residual quantity of at least one process medium used in the treatment device, as at least one system parameter. If for example a prescribed age, i.e. a shelf-life or use-by date, of an ethanol solution is exceeded, its water content may possibly be above the desired value (hygroscopic effect). Certain solutions used in an embedding device or automatic staining device also have best-before dates. These best-before dates can be detected in the device (for example through a bar code or RFID chip) and stored there. Once the best-before date of the corresponding process medium has nearly been reached, and optionally taking account of a detected temperature, this is indicated by the "amber" display state of the traffic light function. Once the best-before date has passed, a red display is shown. Similarly, the display function may also be used for notification of whether a supply of process medium has almost been used up ("amber") or entirely used up ("red") and therefore has to be replaced. The consumption of a process medium can be determined by calculating the length of time until it is used up, after it has been replaced (e.g. new processor kit containing a solution or a staining agent) by means of the quantity and average consumption rate. Alternatively, it is also, of course, possible to detect the fullness level.

In particular, it is advantageous to document problems and faults and their remedies in an automatic treatment device. It is then possible to tell precisely when particular samples were treated and with which process medium. At a later time this provides evidence of a satisfactory run. At the same time it is also possible to document whether certain treated objects were subjected to a problematic or critical system state.

Particularly advantageously, within the scope of the method according to the invention, it is also possible to determine a temperature of at least one process medium used in the treatment device and/or of at least one system component. For example, the infiltration of histological samples is routinely carried out with paraffin wax maintained at a specified temperature, as already mentioned. If the temperature falls below this level the infiltration capacity of the paraffin wax is reduced, which can also be indicated by a display of "amber", or, if there is a sharp deviation, "red". If a desired temperature is exceeded, damage might occur to the embedding medium or the sample material, and this is also indicated accordingly.

In this context it may prove particularly advantageous if at least one sample state of samples being processed in the treatment device is determined and indicated. This may advantageously be the retention time of samples. If for reasons which are not necessarily known the duration of one of the above-mentioned steps is exceeded, this can also be notified to the user in the form of the traffic light function.

As already mentioned, a display system for a treatment device which is configured for carrying out the method and a corresponding treatment device are also the subject of the invention. For features and advantages of the display system and treatment device, to avoid repetition, reference is expressly made to the method features already described.

In particular, a display system according to the invention comprises screen indicator means as means for representing the classified system state, by means of which the invention can be implemented to a particular advantage in existing treatment devices (possibly retro-fitted).

Further advantages and embodiments of the invention will become apparent from the specification and the attached drawings.

It will be understood that the features mentioned above and those still to be explained may be used not only in the particular combination specified but also in other combinations or on their own without departing from the scope of the present invention.

The invention is schematically represented in the drawings by means of an embodiment by way of example and is described in detail hereinafter with reference to the drawings. The embodiment shown relates to an automatic embedding device, but the invention is not to be restricted to this. As already emphasised several times, the invention is also suitable for an automatic staining device or an automatic covering device and also relates expressly to these devices. Moreover, as also previously mentioned, the invention is also suitable for combinations of two or more such pieces of equipment, such as an embedding device, automatic staining device and automatic covering device, and refers expressly to such combinations. Purely in the interest of clarity the invention is hereinafter described with reference to one of these devices, namely an embedding device.

BRIEF DESCRIPTION OF THE DRAWINGS

The invention is schematically illustrated in the drawings by means of an embodiment by way of example and is described in detail hereinafter with reference to the drawings, in which.

DETAILED DESCRIPTION OF THE INVENTION

Figure 1:
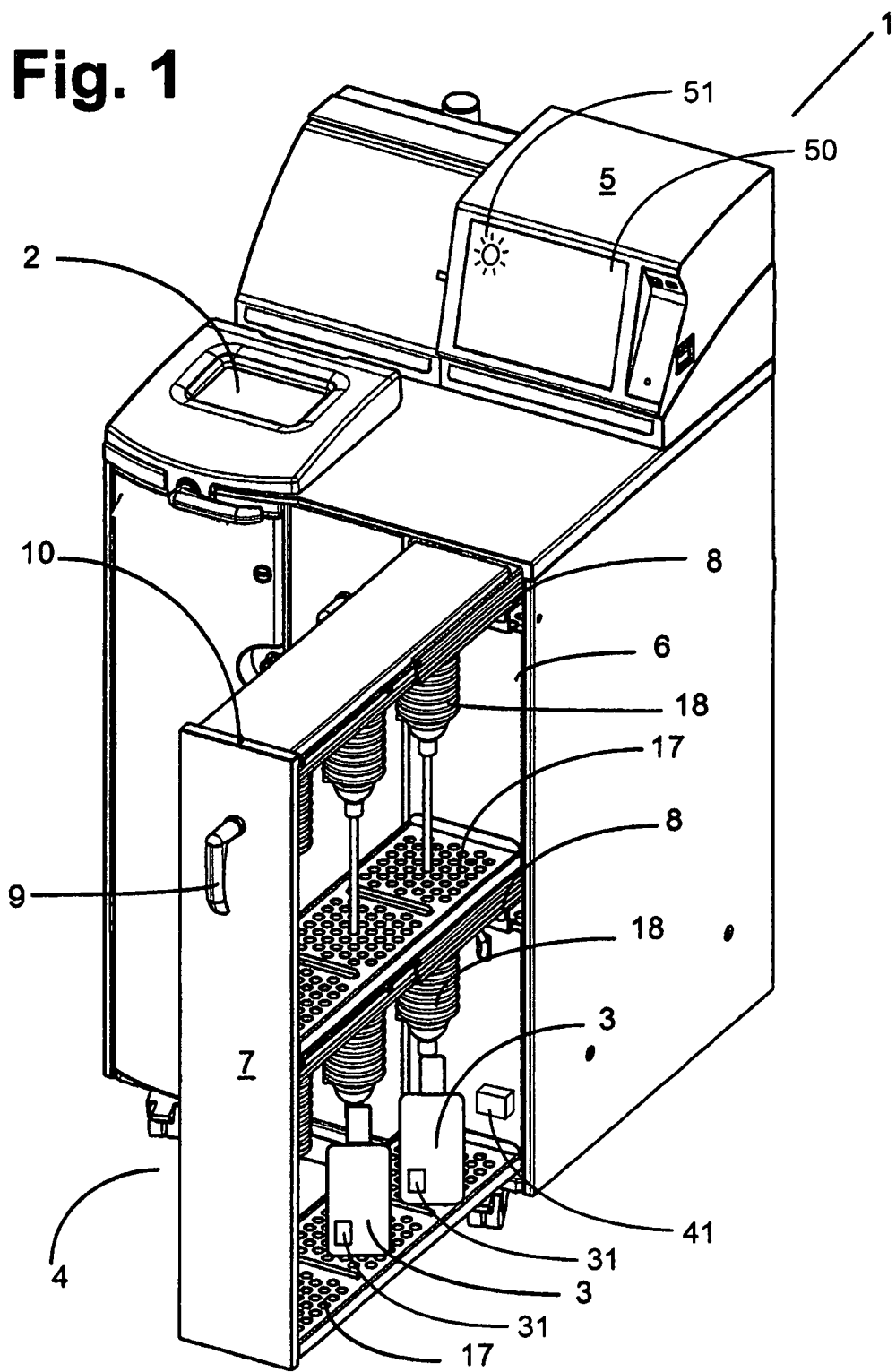
FIG. 1 shows an embedding device which comprises a display system according to a particularly preferred embodiment of the invention.

FIG. 1 shows an embedding device in the form of a tissue processor 1. The tissue processor 1 comprises a retort 2 for processing samples and a control device 5. The tissue processor 1 is equipped with a pull-out device 4 which is connected to the housing of the tissue processor 1 by means of telescopic rails 8. The pull-out device 4 has two floors 17 arranged one above the other as a support for a plurality of containers 3 for process media or supplies of reagent, a closed front 7 and two freely accessible sides 6. Through the side 6 it is possible to gain free access to the container of reagent 3 in order to exchange it. The reagent supply containers 3 are each connected via a connecting piece 18 to a transporting system by means of which the reagents used are conveyed from the reagent supply containers 3 into the retort 2 and back again.

Mounted on the front 7 of the pull-out device 4 is a pivotable lever 9 which is mechanically connected to a latching bolt 10 for latching the pull-out device 4 in the housing of the tissue processor 1. The lever 9 simultaneously acts as a handle for moving the pull-out device 4.

The control device 5 has a display 50 on which an error button 51 is displayed. The error button 51 in this embodiment shows the colours red, amber or green, depending on a display state of a traffic light function, or alternates between different display states, as already explained previously. Instead of a single button it is obviously also possible to provide a known traffic light display with three colour fields which are activated and/or lit up depending on the traffic light function.

The error button 51 may, for example, indicate whether a reagent in a reagent supply container 3 has been almost or totally used up or whether the pull-out device 4 of the tissue processor 1 has been opened, in a manner that is not permitted. The storage containers 3 may for example comprise sensors 31 by means of which a purity, a temperature and/or a concentration of the process media contained therein can be determined and evaluated. Generally known sensors for determining temperature or concentration values such as, for example, photometric, conductor metric and/or potentiometric measuring sensors may be used, possibly in combination. It is also possible to detect a temperature and/or contamination of the air (e.g. by xylene) inside the pull-out device 4, as indicated by a sensor 41.

Figure 2:
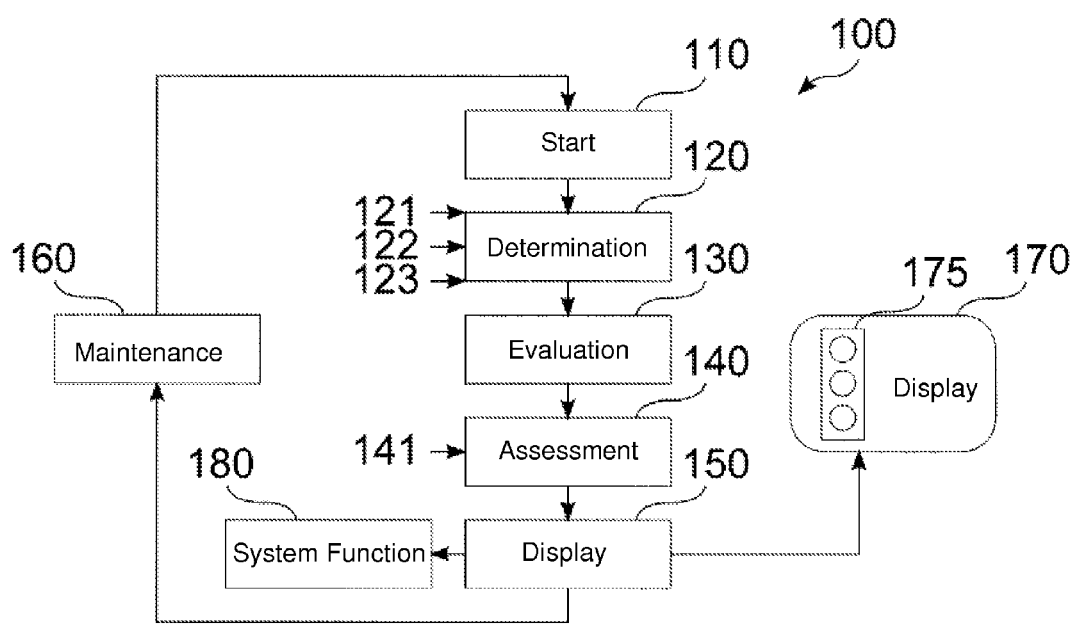
FIG. 2 shows a method taking place according to a particularly preferred embodiment of the present invention.

FIG. 2 shows a process which takes place according to a particularly preferred embodiment of the invention, schematically shown, and generally designated 100.

The method advantageously takes place in a cyclical manner, particularly on the basis of a diagnostic or system cycle, while a maintenance function 160 or a corresponding maintenance step 160 can be implemented. At beginning 110 of each cycle the process is in a basic state. In step 120, system parameters are determined which are illustrated by entries 121-123. As explained previously, the system parameters are evaluated in step 130, for example classified and/or graded into criticality stages.

In step 140 the system state is evaluated on the basis of at least one system parameter evaluated in step 130. In step 140, further inputs 141, for example system values or user inputs, can also be taken into account. The further inputs may also be used, in particular, to influence the evaluation of the system state, while as already mentioned particular sample properties or sample requirements, for example, can be taken into account. In step 150, the system state evaluated is displayed by means of a traffic light function which comprises corresponding display states, preferably in the form of a corresponding traffic light display 175, preferably on a display 170.

At the same time, for example if a systems state is judged to be critical, a system function 180, for example an emergency stop and/or an alarm function, can be initiated.

In particular it is useful to store the system state that has been detected and evaluated for documentation purposes, after going through a diagnosis loop, for example in the maintenance step 160. The data to be stored contains, in particular, information as to the nature and state of the process media used and the samples that pass through the treatment device. In this way it is possible to document precisely, even at a later stage, with regard to a specific sample, which processes this sample has undergone, and with which process media.

The invention is not to be limited to the specific embodiments disclosed, and modifications and other embodiments are intended to be included within the scope of the invention.

LIST OF REFERENCE NUMERALS

1 Treatment device, embedding device
2 Retort
3 Reagent storage container
4 Pull-out device
Control device
6 Side of pull-out
7 Front of pull-out
8 Telescopic rails
9 Pivot lever
10 Locking bolt
17 Support floor
18 Connecting piece
50 Display
51 Error button
100 Display process
110 Start
120 Determination
121, 122, 123 Entries
130 Evaluation
140 Assessment
141 Further inputs
150 Display
160 Maintenance step
170 Display
175 Traffic light display
180 System function

The invention claimed is:

1. Method for displaying a system state of an automatic treatment device (1) performing a plurality of process steps for microscopic samples based on system parameters (121, 122, 123) of the treatment device (1), the displaying method comprising:
  a) determining (120) at least one system parameter (121, 122, 123),
  b) evaluating (130) the at least one determined (120) system parameter (121, 122, 123) based on evaluation criteria,
  c) evaluating (140) the system state based on the at least one evaluated (130) system parameter (121, 122, 123), and
  d) displaying (150) the evaluated (140) system state by a traffic light function (175) having display states, the display spanning the process steps, wherein an error button (51) is provided with the traffic light function (175) or the traffic light function (175) is in the form of an error button (51) being configured either separately or on a monitor display (50), wherein, by selecting the error button (51), one or more of the following is displayed: information relating to the evaluated system state and/or information relating to the associated process step.

2. Method according to claim 1, wherein the evaluation (140) of the system state comprises classification of the system state into at least two evaluation categories.

3. Method according to claim 2, wherein the traffic light function (175) has a number of display states which correspond to a number of evaluation categories.

4. Method according to claim 1, wherein the traffic light function (175) is used in which at least some of the display states correspond to one or more of the following displayed colours: red, amber and green, and/or shades of grey.

5. Method according to claim 1, wherein the display states comprise intermediate states corresponding to one or more of the following: flashing and/or simultaneous display of a plurality of colours or mixed colours or intermediate colours or intermediate shades of grey.

6. Method according to claim 1, wherein one or more of the following: a purity and/or concentration of at least one process medium used is determined as the at least one system parameter (121, 122, 123).

7. Method according to claim 1, wherein one or more of the following: an age and a residual amount of at least one process medium used, is determined as the at least one system parameter (121, 122, 123).

8. Method according to claim 1, wherein one or more of the following's determined as the at least one system parameter (121, 122, 123): a temperature of at least one process medium used and a temperature of at least one system component.

9. Method according to claim 1, wherein at least one sample state of a sample processed in the treatment device is determined as the at least one system parameter (121, 122, 123).

10. Method according to claim 1, wherein the traffic light function (175) is used to show the system parameters (121, 122, 123) in response to a user input.

11. Method according to claim 1, wherein the treatment device (1) comprises at least one device selected from the group of devices consisting of: an automatic embedding device (1), an automatic staining device, and an automatic covering device.

12. Method according to claim 1, wherein the traffic light function (175) is configured with two display states.

13. Method according to claim 1, wherein the traffic light function (175) is produced with precisely one display symbol which may take on different display states, where the display symbol represents a circular or triangular area.

14. Display system for an automatic treatment device (1) performing a plurality of process steps for microscopic samples, which is configured according to claim 1.

15. Display system for an automatic treatment device (1) performing a plurality of process steps for microscopic samples, by means of which a system state of the treatment device (1) can be represented based on system parameters (121, 122, 123) of the treatment device, which comprises:
 a) means (31, 41) for determining (120) at least one system parameter (121, 122, 123),
 b) means for evaluating (130) at least one determined (120) system parameter (121, 122, 123) based on evaluation criteria,
 c) means for evaluating (140) the system state based on at least one evaluated (130) system parameter (121, 122, 123), and
 d) means (50, 51) for displaying the evaluated (140) system state in the form of a traffic light function (175), the display spanning the process steps;
 wherein as means (50, 51) for displaying the classified system state and/or the associated process step, either a separately formed error button or an error button (51) on a monitor display (50) is provided, the error button (51) being produced with the traffic light function or the traffic light function (175) being produced in the form of an error button (51).

16. Display system according to claim 15, wherein in order to represent the classified system state the monitor display (50) displays one or more display symbols, particularly in the form of a circle or triangle.

17. Treatment device (1) for performing a plurality of process steps for microscopic samples, the treatment device comprising a display system, wherein the display system comprises:
 a) means (31, 41) for determining (120) at least one system parameter (121, 122, 123),
 b) means for evaluating (130) at least one determined (120) system parameter (121, 122, 123) based on evaluation criteria,
 c) means for evaluating (140) the system state based on at least one evaluated (130) system parameter (121, 122, 123), and
 d) means (50, 51) for displaying the evaluated (140) system state in the form of a traffic light function (175), the display spanning the process steps;
 wherein as means (50, 51) for displaying the classified system state and/or the associated process step, either a separately formed error button or an error button (51) on a monitor display (50) is provided, the error button (51) being produced with the traffic light function or the traffic light function (175) being produced in the form of an error button (51).

18. Device according to claim 17, wherein the treatment devices comprises at least one device selected from the group of devices consisting of: an automatic embedding device (1), an automatic staining device, and an automatic covering device.

* * * * *